US00PP08369P

United States Patent [19]

Suzuki

[11] Patent Number: Plant 8,369

[45] Date of Patent: Sep. 14, 1993

[54] ROSE PLANT-KEIREB VARIETY

[75] Inventor: Seizo Suzuki, Tokyo, Japan

[73] Assignee: The Conard-Pyle Company, West Grove, Pa.

[21] Appl. No.: 909,651

[22] Filed: Jul. 7, 1992

[51] Int. Cl.[5] ..... A01H 5/00

[52] U.S. Cl. ..... Plt./20

[58] Field of Search ..... Plt. 20

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive double red blossoms. The blossoms are Cardinal Red and are widely suffused with Cherry Red. Such blossoms are long lasting when cut and placed in a vase. The plant exhibits an upright growth habit, vigorous vegetation, and is particularly well suited for cut flower production. When forced under greenhouse conditions, the new variety continuously produces long-stemmed flowers throughout the year. Also, the new variety is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meifikalif variety (nonpatented in the United States) and the male parent (i.e., the pollen parent) was the Red Sandora variety (nonpatented in the United States). The parentage of the new variety can be summarized as follows:

Meifikalif × Red Sandora.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long lasting double flowers which are Cardinal Red and widely suffused with Cherry Red,
(b) exhibits an upright growth habit,
(c) exhibits vigorous vegetation,
(d) is well adapted to greenhouse forcing and continuously produces long-stemmed flowers throughout the year under such growing conditions, and
(e) is not particularly affected by cryptogamic diseases.

The new variety well meets the needs of the horticultural industry for a number of uses and is particularly well suited for cut flower production.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the Keireb variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
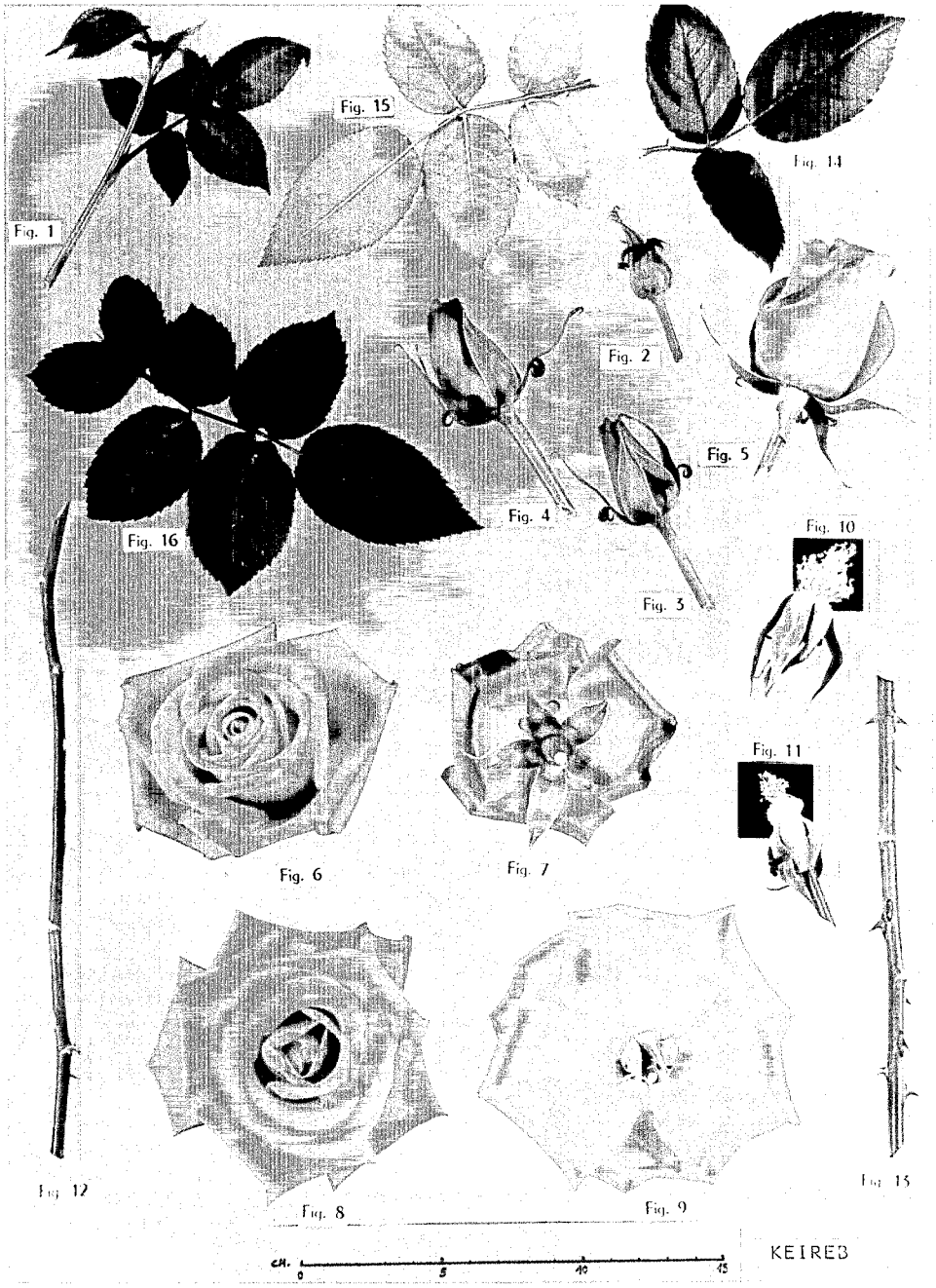
FIG. 1 illustrates a specimen of young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on the observation of two year old plants made during June while budded on *Rosa indica* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 50 to 80 cm. When grown in the field at Wasco, Calif., at the end of one growing season, the average plant height is approximately 1.3 to 1.5 m.

*Habit.*—Upright.

Branches:

*Color.*—Young stems: light green, Green Group 143B. Adult wood: medium green, Green Group 143A.

*thorns.*—Size: medium to large. Quantity: average. Color: pinkish on young stems and pinkish green on adult wood.

Leaves:

*Stipules.*—Adnate, pectinate, and linear.

*Petioles.*—Upper surface: striped reddish brown on young foliage and medium green on adult foliage with more or less glandular edges. Under surface: light green, bear very few prickles.

*Leaflets.*—Number: 3, 5 (most often), and 7. Shape: elliptic. Serration: single and regular. Texture: very consistent. General appearance: dense and bright. Color (young foliage): Upper surface: medium green, Green Group 143A. Under surface: greyish-green, Greyed-Green Group 191A, and widely suffused with reddish coloration. Color (adult foliage): Upper surface: dark green, Green Group 137A. Under surface: medium green, Green Group 138B.

Inflorescence:

*Number of flowers.*—Usually one per stem.

*Peduncle.*—Medium green in coloration and more or less glandular. The length is approximately 12 to 14 cm. on average.

*Sepals.*—Upper surface: tomentose, greenish in coloration. Under surface: smooth, medium green in coloration, the outer sepals are more or less appendiculate.

*Buds.*—Shape: conical. Length: approximately 3.5 cm. on average. Size: large. Color upon opening: Upper surface: Guardsman Red, Red Group 45A. Under surface: light Cardinal Red, Red Group 53C.

*Flower.*—Shape: cup-like and fully double. Diameter: approximately 12 cm. on average. Color (when opening begins): Upper surface: Cherry Red, Red Group 46C and widely suffused with Cardinal Red, Red Group 53B. Under surface: Cherry Red, Red Group 46C and widely suffused with Cardinal Red, Red Group 53C. Color (when blooming): Upper surface: light Cardinal Red, Red Group 53C and widely suffused with Cherry Red, Red Group 46C. Under surface: light Cardinal Red, Red Group 53D. Color (at end of opening): Upper surface: light Cardinal Red, Red Group 53C and widely suffused with Cherry Red, Red Group 46C. Under surface: light Cardinal Red, Red Group 53D. Fragrance: none. Lasting quality: long when cut and placed in a vase. Petal number: approximately 25 on average. Texture: very consistent. Petal drop: good. Petal configuration: rounded. Stamen number: approximately 131 on average. Anthers: bright yellow. Filaments: light fuschia in coloration, and of irregular heights. Pistils: approximately 72 on average. Stigmas: strawlike. Styles: very tomentose at base, strawlike with a fuschia top, and more or less twisted. Receptacle: smooth, medium green, in longitudinal section at the dehiscence of the anthers it is wide and in the shape of a pitcher.

Development:

*Vegetation.*—Vigorous.

*Blooming.*—Continuous when forced in a greenhouse for cut flower production.

*Resistance to diseases.*—Good.

*Aptitude to forcing.*—Very good.

I claim:

1. A new and distinct variety of Hybrid Tea rose plant characterized by the following combination of characteristics:

(a) forms in abundance attractive long lasting double flowers which are Cardinal Red and widely suffused with Cherry Red, (b) exhibits an upright growth habit, (c) exhibits vigorous vegetation, (d) is well adapted to greenhouse forcing and continuously produces long-stemmed flowers throughout the year under such growing conditions, and (e) is not particularly affected by cryptogamic diseases;

substantially as herein shown and described.

* * * * *

CM.
0
5
10
15
KEIRES